United States Patent [19]

Fournier et al.

[11] Patent Number: 4,834,149

[45] Date of Patent: May 30, 1989

[54] METHOD OF RECONSTITUTING A HAZARDOUS MATERIAL IN A VIAL, RELIEVING PRESSURE THEREIN, AND REFILLING A DOSAGE SYRINGE THEREFROM

[75] Inventors: Donald J. Fournier, Bethesda; Douglas W. Jacobs-Perkins, Kensington; William R. Tarello, Bethesda, all of Md.

[73] Assignee: Survival Technology, Inc., Bethesda, Md.

[21] Appl. No.: 171,457

[22] Filed: Mar. 21, 1988

Related U.S. Application Data

[62] Division of Ser. No. 70,802, Jul. 7, 1987, Pat. No. 4,768,568.

[51] Int. Cl.[4] .......... A61J 5/00; A61M 5/00; B65B 3/04; B65D 81/32

[52] U.S. Cl. .......... 141/1; 141/27; 141/286; 141/320; 141/329; 206/219; 215/248; 215/DIG. 8; 73/863.71; 73/863.82; 604/86; 604/90; 604/199; 604/405; 604/411; 604/416; 604/905

[58] Field of Search .......... 141/1, 4, 5, 2, 18, 141/19, 21, 25, 26, 27, 312, 329, 330, 319–322, 383, 59, 98, 286; 215/247, 248, 249, 6, 250, DIG. 8; 206/219; 73/863.71, 863.81, 863.82, 863.83, 863.84; 604/82, 86, 89, 90, 191, 199, 206, 403, 405, 411–416, 905

[56] References Cited

U.S. PATENT DOCUMENTS

| | | | |
|---|---|---|---|
| 2,364,126 | 12/1944 | Cantor | 215/247 |
| 2,794,437 | 6/1957 | Tash | 604/415 |
| 3,882,909 | 5/1975 | Ogle | 141/286 |
| 3,993,063 | 11/1976 | Larrabee | 604/414 |
| 4,191,225 | 3/1980 | Ogle | 141/329 |
| 4,196,732 | 4/1980 | Wardlaw | 141/330 X |
| 4,211,588 | 7/1980 | Raines | 156/73.1 |
| 4,312,349 | 1/1982 | Cohen | 604/406 |
| 4,457,749 | 7/1984 | Bellotti et al. | 604/411 |
| 4,552,277 | 11/1985 | Richardson et al. | 215/249 |
| 4,564,054 | 1/1986 | Gustavsson | 141/329 |
| 4,576,211 | 3/1986 | Valentini et al. | 141/329 |
| 4,582,207 | 4/1986 | Howard et al. | 215/247 |
| 4,588,403 | 5/1986 | Weiss et al. | 604/411 |
| 4,589,879 | 5/1986 | Pearson | 604/411 |
| 4,600,040 | 7/1986 | Naslund | 141/98 |
| 4,607,671 | 8/1986 | Aalto et al. | 141/329 |
| 4,619,651 | 10/1986 | Kopfer et al. | 604/415 |
| 4,645,073 | 2/1987 | Homan | 206/219 |
| 4,671,331 | 6/1987 | Pruden | 141/98 |
| 4,673,404 | 6/1987 | Gustavsson | 604/411 |
| 4,768,568 | 9/1988 | Fournier et al. | 141/286 |

OTHER PUBLICATIONS

The New England Journal of Medicine, vol. 313, No. 19, Nov. 7, 1985, "A Study of Occuptational Exposure to Antineoplastic Drugs and Fetal Loss in Nurses", pp. 1173–1178.

The New England Journal of Medicine, vol. 313, No. 19, Nov. 7, 1985, Editorial, pp. 1220–1221.

*Primary Examiner*—Ernest G. Cusick
*Attorney, Agent, or Firm*—Cushman, Darby & Cushman

[57] ABSTRACT

A method of utilizing an apparatus of the type comprising a vial container hazardous material in the vial container in a condition requiring a diluent to be mixed therewith to form the liquid solution, and an assemblage carried by the vial container for providing (1) a sealed medicament chamber within the vial container within which the hazardous material is disposed, (2) a filter vented control chamber and (3) a sealed variable volume control chamber between the vented control chamber and the medicament chamber. The method is such as to enable an open end of a syringe needle of a diluent syringe having a syringe chamber containing diluent in communication therewith to be moved into and withdrawn successively from the chambers so as to mix the diluent with the hazardous material. The method also contemplates procedures for separately refilling a dosage syringe and for relieving any residual pressure in the vial chamber with the use of an empty syringe prior to initial or final refilling of a dosage syringe. The reconstituting, pressure relief and/or refilling procedures all being performed in such a way as to substantially prevent the hazardous material from entering the immediate atmospheric environment.

9 Claims, 3 Drawing Sheets

METHOD OF RECONSTITUTING A HAZARDOUS MATERIAL IN A VIAL, RELIEVING PRESSURE THEREIN, AND REFILLING A DOSAGE SYRINGE THEREFROM

This is a division of application Ser. No. 070,802, filed July 7, 1987, now U.S. Pat. No. 4,768,568.

This invention relates to the packaging of hazardous material and more particularly to the packaging of such materials which enable a user to mix a diluent with the hazardous material and then fill a syringe with the solution in such a way as to substantially prevent the hazardous material from entering the immediate atmospheric environment.

While the present invention is applicable to hazardous materials in general, the specific example of hazardous materials to which the invention is particularly applicable are freeze dried or powdered cytotoxic drugs such as are used extensively in chemotherapy treatment of cancer patients and radiographic materials.

Freeze dried or powdered cytotoxic drugs are usually contained within a vial of the type which is open ended and has an elastomeric stopper assembly disposed in sealing relation within the open end so as to enable the freeze dried or powdered cytotoxic drug to be sealingly contained therein. The elastomeric stopper assembly is adapted to receive therethrough a needle of a diluent containing syringe. The amount of freeze dried or powdered cytotoxic drug within the vial is an amount such that when dissolved in a proper amount of diluent within the vial the solution has a volume substantially less than the volume of the sealed interior of the vial. Nevertheless, when the diluent is injected into the vial through the needle by the operation of the diluent containing syringe there is sufficient volume of solution within the vial to displace the gas therein into a smaller volume and hence to increase its pressure. It is generally well known that this increase in pressure may cause an aerosol effect when the needle is removed. This aerosol effect may result in the passage outwardly through the elastomeric stopper assembly of portions of the cytotoxic drug in the form of aerosol or droplets. This aerosoling action presents a highly dangerous situation to the nurse or other personnel reconstituting the cytotoxic material with a diluent.

The extent to which this aerosoling will occur is basically determined by whether or not the diluent syringe which is utilized to inject the diluent into the vial is used as the injectate syringe as well and, if so, whether or not the injectate syringe is to be filled with injectate before being withdrawn from the vial. The minimal extent of aerosoling is presented in the case of the one dosage vial where the injection of the diluent into the vial, the subsequent mixing of the diluent with the powder in the vial, and the subsequent refilling of the mixture of the diluent and powder back into the syringe all take place without the necessity to remove the syringe needle from the elastomeric stopper of the vial until after the single dosage has been refilled into the syringe chamber. The procedure inevitably results in leaving some liquid in the vial so that the pressure in the vial does not completely reduce to atmospheric pressure after refilling. Consequently, even under these most advantageous circumstances small existing pressure at the time of needle removal after refilling can result in some aerosoling. The usual procedure to accomplish this most favorable operation is to penetrate the needle through the elastomeric stopper while the vial is upright and then press on the syringe plunger. As the diluent is injected into the vial the pressure in the vial as well as the pressure acting on the plunger increases. To accomplish the mixing operation, the operator has two options, he can keep the plunger depressed so as to maintain the increased pressure condition or he can allow the plunger to retract to fill the syringe chamber with gaseous fluid. In either event, it may become necessary to shake the vial to achieve full mixing. The term "gaseous fluid" as used in the present context means the air and/or other gas in the vial container above the liquid solution after the diluent has been added and any hazardous material suspended in the air in the form of particulate solids, vapor and/or liquid and any associated diluent similarly suspended.

After mixing has been accomplished, refilling of the syringe chamber with the reconstituted liquid medicament solution requires that the syringe plunger be fully engaged within the syringe chamber and that the syringe and vial be inverted so that the liquid in the vial is above the open end of the syringe needle extending just through the elastomeric stopper. Another favorable aspect of this most advantageous manner of proceeding is that the increased pressure conditions within the vial above the liquid materially aids in filling the syringe chamber. That is, it is not necessary for the operator to draw the liquid out of the vial with the syringe, rather, the positive pressure within the vial tends to cause the liquid to flow into the syringe chamber without pulling back on the plunger. Nevertheless between the time that extrusion of the diluent into the vial takes place and the time when refilling is complete, the syringe and vial are manipulated at times when maximum pressure conditions exist in the vial with the resultant possibility of leakage between the exterior periphery of the syringe needle and the interior periphery of the elastomeric stopper accommodating the needle penetration.

There are many situations where this most favorable method of operation cannot be utilized. For example, in many hospital situations, the reconstituting of the drug must be performed in the pharmacy remote from and at a time prior to the actual use of the reconstituted drug in the ward or patient's room. Thus, in any situation where reconstitution is divorced from subsequent use, the possibility exists that reconstitution will be accomplished by simply withdrawing the syringe needle from the elastomeric stopper with the plunger fully engaged within the syringe chamber so that pressure conditions within the vial are maximum at the time of withdrawal. This needle withdrawal under maximum pressure conditions is sometimes avoided by simply relaxing the plunger prior to withdrawal and allowing the syringe chamber to fill with the gaseous fluid on top of the liquid in the upright vial. This practice heretofore has been a source of contamination when the gaseous fluid contents of the syringe are subsequently discharged into the immediate environment in cases where the syringe is to be reused.

In the case of multidosage vials, almost by definition the reconstituting procedures are divorced from the use procedures. Consequently, all of the problems of effecting a separate reconstituting procedure with a single dosage vial are simply multiplied.

Another handling procedure which presents a potential cytotoxic material contact with the user exists when the injecting syringe is finally prepared for injecting. The actual step of filling the injecting syringe with cytotoxic material solution almost inevitably results in the inclusion of some air being taken within the syringe. In the more common usage wherein the cytotoxic material solution is to be injected into an i.v. bag, the expelling of this air before injection is not critical. Where the hazardous material is to be directly injected into the patient, particularly intravenously (e.g. some radiographic materials) air should be expelled or extruded from the syringe before the actual injection is performed. The air is extruded by operating the syringe with the needle end uppermost in a direction to extrude the contents. Here again, it is almost inevitable that some of hazardous material solution will be extruded from the needle end of the syringe along with the last pocket of air.

Recent studies have shown that the effects of exposure to anti-neoplastic drugs including cytotoxic agents can be quite severe. Particularly this is true when the exposure is on a day-to-day basis over an extended period. A definite cause and effect relationship between exposure and fetal loss has been observed in a study reported in the Nov. 7, 1985 issue of The New England Journal of Medicine entitled "A Study of Occupational Exposure to Antineoplastic Drugs and Fetal Loss in Nurses" (Vol. 311, No. 19, pages 1173–1178). See also the Editorial in the same edition, pages 1220–1221.

Presently, there is only one procedure available for protecting the user to the extent of enabling the user to accomplish both the reconstituting and air expelling operations without exposing the cytotoxic drugs to the immediate atmospheric environment. This method involves the use of the so-called glove box where the user inserts his hands into gloves so that the user can manipulate the syringe or syringes and the vial with the gloves within an enclosed space. This procedure is bothersome and somewhat cumbersome to perform.

A second presently available procedure which is capable of preventing aerosoling is to use a dispensing pin of the type disclosed in U.S. Pat. No. 4,211,588. The dispensing pin constitutes a separate device which functions to enable diluent to be extruded into the vial and hazardous material solution to be aspirated out of the vial while the interior of the vial is maintained at atmospheric pressure. The use of the dispensing pin obviates the problem of aerosoling since the elastomeric stopper of the vial is never pierced by a needle but rather only by a pin having two parallel passages extending therethrough. One of the passages functions to maintain the interior pressure within the vial substantially at atmospheric pressure by venting the one passage to atmosphere through a filter. The other passage functions as a conduit for conducting diluent into the vial and hazardous material solution out of the vial.

The exterior end of the other passage is formed with an interior luer lock fitting which detachably sealingly engages an exterior luer lock fitting on the injecting syringe with a needle after filling it and removing it from the luer lock of the dispensing pin. After the needle has been secured on the filled injecting syringe, as by engaging the interior luer lock fitting of the needle with the exterior luer lock fitting of the syringe, the user must now operate the syringe to extrude the air from within it with the almost inevitable extrusion of hazardous material solution after the last pocket of air is expelled, as aforesaid. The usual procedure for handling any hazardous material extruded in this procedure is to catch the extrudite in a cloth or other absorbent material and thereafter safely dispose of the soiled cloth or other material. This procedure is cumbersome and inherently fraught with the hazard of environmental and/or accidental exposure to the user.

In addition to the commercially available apparatus described above, the patent literature discloses several other proposed solutions to the problem presented. The expired patented literature; namely, U.S. Pat. No. 2,364,126 discloses an outer cap assembly for securement over a vial closure assembly, the outer cap assembly providing a control chamber over the central elastomeric portion of the closure assembly. Needle access to the chamber can be obtained through a septum provided by the outer cap assembly. The disclosure does not contemplate filtering the chamber to atmosphere nor does it make any reference to the procedure for aspirating air from the syringe used with the outer cap assembly.

U.S. Pat. No. 3,882,909 discloses in FIG. 7 an apparatus similar to that disclosed in U.S. Pat. No. 4,211,588 noted above except that the dual passage pin is straight and the upper ends of the pin and passages are surrounded by a chamber having a septum in the upper end thereof and a parallel vent with a filter therein. U.S. Pat. No. 4,588,403 discloses a functionally similar apparatus with a different structural arrangement.

U.S. Pat. No. 4,564,054 discloses the equivalency between a communicating chamber vented through a filter and a communicating chamber vented to a bladder (see also U.S. Pat. No. 4,600,040). This patent also discloses an embodiment in FIG. 14 wherein a simple exterior non-communicating chamber similar to that provided in expired U.S. Pat. No. 2,364,126 is provided with a filtered vent. Stated differently, the FIG. 14 embodiment is the same as U.S. Pat. No. 2,364,126 with the chamber vented through a filter to atmosphere, as disclosed in U.S. Pat. No. 3,882,909.

U.S. Pat. No. 4,619,651 discloses in FIG. 7 an exterior chamber vented to atmosphere through a filter. However, there are many other embodiments described in this patent in which the chamber provided is simply a closed chamber either exteriorly of or within the neck of the vial. Other pertinent patent literature disclosures may be found in U.S. Pat. Nos. 4,552,277 (telescoping closed chamber), 4,576,211 (telescoping closed chamber with special needle), and 4,582,207 (simple closed chamber).

In summary, it can be stated that in those instances where a continuously communicating chamber is provided, aerosoling is minimized by insuring an interior atmospheric pressure within the vial whenever the needle is withdrawn from the elastomeric stopper; however, the advantages of loading the syringe under pressure are lost. Where a non-communicating chamber is provided, the advantages of loading under pressure are retained; however, the chamber must be operable to accommodate aerosoling when the needle is removed from the vial and thereafter prevent aerosoling when the needle is removed from the chamber. Where the chamber is a simple closed chamber, the pressure within the chamber will increase in response to aerosoling when the needle is withdrawn from the vial so that the withdrawal of the needle from the chamber will take place with the chamber contaminated and under pressure so that aerosoling to the atmospheric environment becomes a likelihood. The use of a filtered vent in the chamber prevents an elevated chamber pressure so long as the filter does not become blocked. Efforts to make the chamber expansible so as to prevent an elevated pressure within the chamber are severely limited by the extent of the expanded volume which can be practically accommodated.

An object of the present invention is to provide apparatus which achieves the advantages of pressure filling while at the same time providing for controlled needle withdrawal from the control chamber under atmospheric pressure conditions by virtue of a filtered vent opening therein while at the same time positively preventing the filtered vent opening from coming into contact with the saturated vapor of the gaseous fluid which may aerosol when the needle is withdrawn from the vial. In accordance with the principles of the present invention, this objective is accomplished by providing apparatus which includes a vial container having hazardous material therein in a condition requiring a diluent to be mixed therewith to form a liquid solution. An assemblage is carried by the vial container which provides (1) a sealed medicament chamber within the vial container within which the hazardous material is disposed, (2) a vented control chamber and (3) a sealed control chamber between the vented control chamber and the medicament chamber. A vent opening communicates the vented control chamber to the atmosphere and a hydrophobic filter is disposed in cooperating relation with the vent opening for enabling the pressure within the vented control chamber to remain at atmospheric conditions while preventing movement of hazardous material outwardly through the vent opening. A movable piston is operable in response to the communication of fluid pressure within the sealed control chamber to expand the volume of the sealed control chamber within limits to retain the fluid pressure communicated therein at atmospheric conditions. Resilient materials forming parts of the chambers function to enable an open end of a syringe needle of a diluent syringe having a syringe chamber containing diluent in communication therewith to be moved successively (1) into the vented control chamber, (2) out of the vented control chamber into the sealed control chamber and (3) out of the sealed control chamber into communicating relation with the medicament chamber in such a way that a substantial seal is maintained between the exterior periphery of the syringe needle (1) at the position of entry into the vented control chamber (2) at the position of passage out of vented control chamber and into the sealed control chamber and (3) at the position of passage out of the sealed control chamber and into the medicament chamber whereby ejection of the diluent in the syringe chamber through the open end of the diluent syringe needle while in communication with the medicament chamber results in the establishment of a liquid solution of diluent and hazardous material and a gaseous fluid containing saturated vapor of the hazardous material solution within the medicament chamber both under elevated pressure conditions which enable the diluent syringe chamber to be readily recharged with gaseous fluid from the medicament chamber thus reducing the pressure conditions of the gaseous fluid within the medicament chamber and syringe chamber and the liquid solution in the medicament chamber to a value near atmospheric conditions. The resilient materials further function to enable the open end of the diluent syringe needle to be withdrawn successively (1) out of the medicament chamber and into the sealed control chamber (2) out of the sealed control chamber and into the vented control chamber and (3) out of the vented control chamber in such a way that the substantial seals with the exterior periphery of the syringe needle at the positions aforesaid become effectively self-sealing so that during the aforesaid syringe needle withdrawal (1) any passage of gaseous material from the medicament chamber exteriorly of the syringe needle by virtue of pressure differential is received and sealed within the sealed control chamber and (2) the gaseous fluid in the syringe chamber can be ejected therefrom through the open end of the syringe needle into the vented control chamber.

Another object of the present invention is to provide the apparatus described above by the provision of a separate control assembly which is cooperable with a conventional vial. In accordance with the principles of the present invention, this objective is realized by providing a hollow control structure having opposite first and second open ends. The first open end of the control structure is closed by a septum capable of having the syringe needle moved in penetrating relation therethrough and of providing a seal after the syringe needle has been withdrawn. An attaching assembly is provided on the control structure for fixedly securing the control structure to a vial so that the second open end thereof is disposed in sealed relation to the stopper assembly end thereof. A pressure containing piston within the hollow interior of the control structure between the open ends thereof divides the hollow interior into a vented chamber communicating with the septum through the first open end and a sealed chamber communicating with the central exterior of the elastomeric stopper assembly of the vial through the second open end. The control structure has a vent opening therein which communicates the vented chamber to the atmosphere. A filter is disposed in cooperating relation with the vent opening for enabling the pressure within the vented chamber to remain at atmospheric conditions while preventing movement of hazardous material outwardly through the vent opening. The piston is mounted for movement in response to the increase of pressure conditions within the sealed chamber while the vented chamber is retained under atmospheric pressure conditions by the vent opening from an initial position wherein the volume of the vented chamber is maximum and the volume of the sealed chamber is minimum to a final position wherein the volume of the vented chamber is minimum and the volume of the sealed chamber is maximum. The piston is capable of having the syringe needle which is first moved in penetrating relation through the septum thereafter moved in penetrating relation therethrough and of providing a seal after the syringe needle has been withdrawn so that when the syringe needle after having been moved in penetrating relation successively through the septum and the piston is thereafter moved in penetrating relation through the elastomeric stopper assembly any elevated pressure conditions and aerosoling of hazardous material which passes outwardly of the elastomeric stopper assembly incident to syringe needle withdrawal therefrom is captured within the sealed chamber and any elevated pressure conditions produced thereby are reduced substantially to atmospheric conditions by the increase of the volume thereof through movement of the piston from the initial position until the same reaches the final position so that the subsequent withdrawal of the syringe needle from the piston occurs while the sealed chamber is under atmospheric pressure conditions and hence no aerosoling of hazardous material into the vented chamber occurs incident to such withdrawal thereby enabling the subsequent withdrawal of the syringe needle from the septum to occur under uncontaminated atmospheric pressure conditions within the vented chamber.

Another object of the present invention is the provision of an improved method of using a control assembly of the type adapted to be mounted on a vial so as to provide a septum sealed control chamber capable of receiving a volume of hazardous material containing gaseous fluid under pressure through the elastomeric stopper of the vial and of retaining the gaseous fluid substantially at atmospheric pressure conditions and hence no aerosoling of hazardous material into the vented chamber occurs incident to such withdrawal thereby enabling the subsequent withdrawal of the syringe needle from the septum to occur under uncontaminated atmospheric pressure conditions within the vented chamber.

Another object of the present invention is the provision of an improved method of using a control assembly of the type adapted to be mounted on a vial so as to provide a septum sealed control chamber capable of receiving a volume of hazardous material containing gaseous fluid under pressure through the elastomeric stopper of the vial and of retaining the gaseous fluid substantially at atmospheric conditions and preventing the hazardous material from passing outwardly of the control chamber. The method is applicable not only to the use of the improved control assembly of the present invention which provides a control chamber divided into a vented variable volume chamber portion and a sealed variable volume chamber portion, but to the use of known control assemblies of the type providing a single non-communicating exterior control chamber which is either filter vented or vented to a bladder so as to provide for the controlled relief of the interior pressure of a pressurizable vial to atmospheric conditions after reconstitution. The method of the present invention serves to materially lessen the problems of control which are presented in the most difficult situations, as aforesaid, where reconstitution is divorced from filling and use. In accordance with the principles of the present invention, this objective is achieved by carrying out the steps set forth below. Communicating the open end of the syringe needle disposed in penetrating relation through the control assembly septum and the vial elastomeric stopper assembly with the gaseous fluid under pressure within the vial chamber with the syringe plunger fully engaged within the syringe chamber, maintaining the communication until the syringe plunger is withdrawn from its fully engaged position into an intermediate position so that sufficient gaseous fluid from the vial chamber passes into the syringe chamber through the open end of the syringe needle to reduce the pressure of the gaseous fluid in the vial chamber and in the syringe chamber to a common pressure which is at most substantially equal to atmospheric pressure, withdrawing the syringe needle from the vial elastomeric stopper assembly while the syringe plunger is maintained in the intermediate position, moving the syringe plunger from the intermediate position into its fully engaged position with the open end of the syringe needle in communicating relation with the control chamber so as to expel the gaseous fluid contents of the syringe chamber through the open end of the syringe needle into the control chamber and withdrawing the syringe needle from the septum.

These and other objects of the present invention will become more apparent during the course of the following detailed description and appended claims.

The invention may best be understood with reference to the accompanying drawings wherein an illustrative embodiment is shown.

DESCRIPTION OF THE PREFERRED EMBODIMENT

Figure 4:
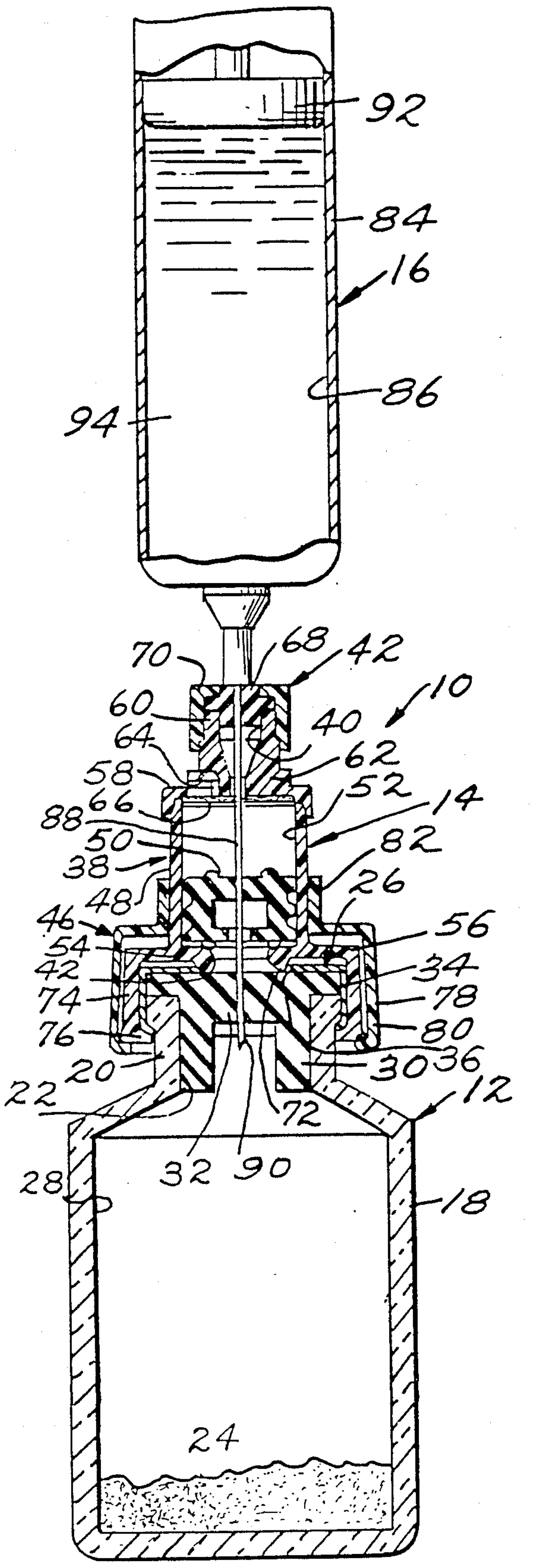
FIG. 4 is a vertical sectional view of the apparatus of the present invention including the control assembly and a hazardous material containing vial, the control assembly and vial being shown in operative mounted relation with respect to one another and to a diluent syringe just prior to the injection of the diluent into the vial.
Figure 5:
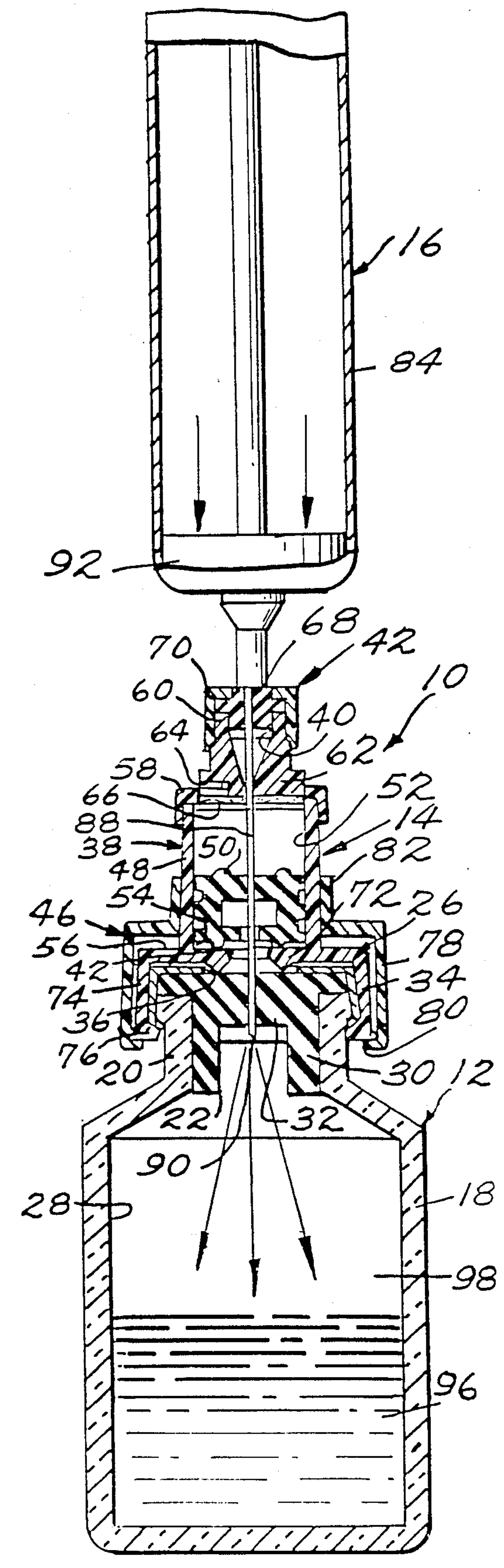
FIG. 5 is a view similar to FIG. 4 showing the operative relationship between the control assembly, vial and diluent syringe after the injection of the diluent into the vial.
Figure 6:
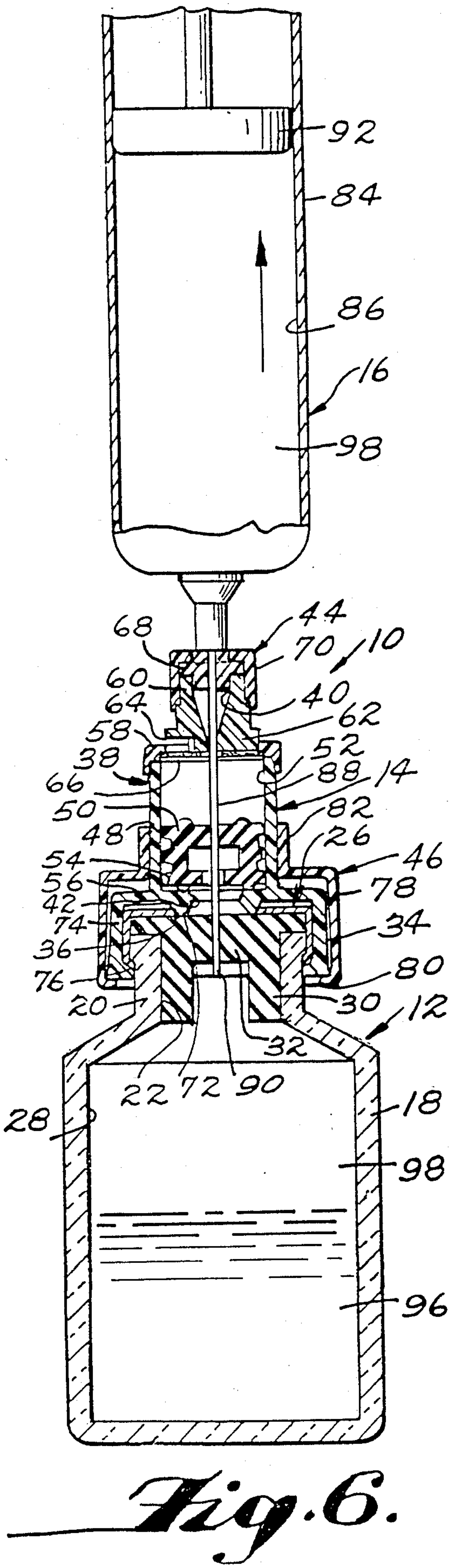
FIG. 6 is a view similar to FIG. 4 illustrating the first steps of the method of relieving the gaseous fluid pressure in the vial after reconstitution in accordance with the principles of the present invention.

Referring now more particularly to the drawings, there is shown in FIGS. 4–6 thereof an apparatus, generally indicated at 10, which embodies the principles of the present invention. The apparatus enables a user to mix a diluent with a hazardous material and then fill a syringe with the solution in such a way as to substantially prevent the hazardous material from entering the immediate atmospheric environment. The apparatus 10 in general includes two basic components, one, a hazardous material package assembly, generally indicated at 12, and the other a control assembly, generally indicated at 14, which is adapted to cooperatively engage the hazardous material package assembly 12 to perform the basic functions noted above. As best shown in FIGS. 4–7, a diluent syringe, generally indicated at 16, is utilized with the control assembly 14 to relieve the gaseous pressure in the package assembly 12 after the mixture of the diluent with the hazardous material within the package assembly 12 has been accomplished, the pressure relief being accomplished in accordance with the method of the present invention so as to prevent hazardous material from entering the immediate atmospheric environment.

The package assembly 12 is essentially a commercial package in the form of a vial which includes a glass container 18 having an exteriorly beaded neck 20 defining an open end 22. A hazardous material 24 is disposed within the vial container 18. As shown, the hazardous material is in the form of a freeze dried or powdered cytotoxic drug (antineoplastic drugs) of the type frequently used in treating cancer. In the package, the cytotoxic drug dosage 24 is preferably in freeze dried or powdered form suitable to be readily dissolved by a diluent to form an injectable liquid solution containing the hazardous material. An elastomeric stopper assembly, generally indicated at 26, functions as a closure assembly for the vial container 18 retaining the cytotoxic material 24 in pressure sealed relationship within the interior of the vial container which constitutes medicament chamber 28.

It will also be noted that the hazardous material 24 is in an amount such that when dissolved in a proper amount of diluent within the vial, the solution has a volume substantially less than the medicament chamber 28 of the vial container 18. All of this is in accordance with conventional practice.

The closure assembly 26 is preferably also constructed in accordance with conventional practice and includes a stopper 30 formed of a suitable elastomeric material. As shown, the stopper includes a main, generally cylindrical slotted body portion which is adapted to engage within and seal off the open end 22 of the vial container 18. Extending radially outwardly from the upper end of the cylindrical portion is a peripheral flange portion which overlies and engages the upper end of the exteriorly beaded neck 20 of the vial container 18. The stopper 30 also includes a central portion 32 which is disposed within the flange portion.

The closure assembly 26 also includes a retainer 34 for engaging the exteriorly beaded neck 20 of the vial container 18 and retaining the elastomeric stopper 30 in closing sealed relation with respect to the open end 22 of the vial. As shown, the retainer 34 is formed of a relatively thin metal element to include a top wall which engages the stopper flange portion and has a skirt portion extending downwardly from its exterior periphery in conformed engagement with the exterior periphery of the flange portion of the elastomeric stopper 30 and the exteriorly beaded neck 20 of the vial container 18. The top wall of the retainer 34 is centrally apertured, as indicated at 36, so as to provide needle access to the central portion 32 of the elastomer stopper 30.

The control assembly 14 includes a hollow housing or control structure, generally indicated at 38, providing opposite open ends 40 and 42. The open end 40 is closed by a septum assembly, generally indicated at 44, and an attaching assembly, generally indicated at 46, is carried by the hollow structure 38 for mounting it on the stoppered end of the vial so that the open end 42 is disposed in sealed communicating relation with the exterior of the central portion 32 of the elastomeric stopper 30.

The hollow structure 38, as shown, is made up essentially of two plastic moldings. The first of these provides a cylindrical wall 48 having an inner cylindrical surface defining the major periphery of a control chamber space between the open ends 40 and 42. In accordance with the principles of the present invention, a movable pressure containing means in the form of a piston 50, preferably made of elastomeric material, is slidably mounted with its exterior periphery in engagement with the cylindrical surface for movement from an initial limiting position, shown in FIG. 1, to a final limiting position. The piston 50 divides the control chamber space defined by the cylindrical surface into two variable volume control chambers 52 and 54. The control chamber 54 is a sealed control chamber which communicates with the open end 42 and is positioned between the medicament chamber 28 and the control chamber 52, which is a vented control chamber.

In its initial limiting position, the piston 50 engages a radially extending annular wall 56 which is integral with the adjacent end of the cylindrical wall 48 and extends both radially inwardly and radially outwardly therefrom. The radially inwardly extending portion of the annular wall 56 provides an upwardly facing surface which engages the piston when in its initial limiting position. The final limiting position is determined by engagement of the piston 50 with a inwardly extending annular section of a first tubular portion 58 of the second plastic molding, the remaining section of which constitutes a cylindrical skirt section which is suitably rigidly secured in surrounding abutting relation with the adjacent end portion of the cylindrical wall 48. The second plastic molding includes a second tubular portion 60 which is connected with the first tubular portion 58 by a plurality of radially extending ribs 62 which define therebetween vent openings 64. The inwardly facing surface of the second tubular portion 60 is formed with a small annular ridge (not shown) constituting an energy director and a second inwardly facing surface of the first tubular portion 58 is formed with a second energy director. The energy directors are utilized to sealingly connect, as by ultrasonic energy, a centrally apertured thin cylindrical filter pad 66 of plastic material in fibrous form so that the filter pad extends over the vent openings 64 and serves to prevent passage of hazardous material 24 outwardly of the vented control chamber 52. The filter pad is preferably hydrophobic and has a pore size of approximately 0.2 microns.

The septum assembly 44 is preferably in the form of a centrally enlarged septum disk 68 engaged upon an annular sealing ridge formed on the upper end of the second tubular portion 60 and retained in sealingly engaged relation therewith by a centrally apertured cap 70 suitably fixed to the second tubular portion 60.

The lower portion of the sealed control chamber 54 communicates with the exterior surface of the central portion 32 of the elastomeric stopper 30 in sealing relation. To this end, a depending annular lip 72 is formed on the inner portion of the radial wall 56 so as to engage with the exterior surface of the stopper 30.

The attaching assembly 46 includes an annular skirt 74 which is integral with and extends downwardly from the outer periphery of the radial wall 56. The skirt 74 terminates in an inwardly directed annual bead 76 for engaging beneath the stopper assembly 26 of the vial 10. When the bead 76 is engaged beneath the stopper assembly 26, the annular lip 72 is urged into sealing engagement with the upper surface of the elastomeric stopper 30. The skirt 74 and bead 76 are formed with a plurality of annularly spaced axial slots which segment the skirt and enable the segments to readily yield outwardly so that the bead 76 can easily snapped over the stopper assembly 26 at the top of the vial 10.

Figure 1:
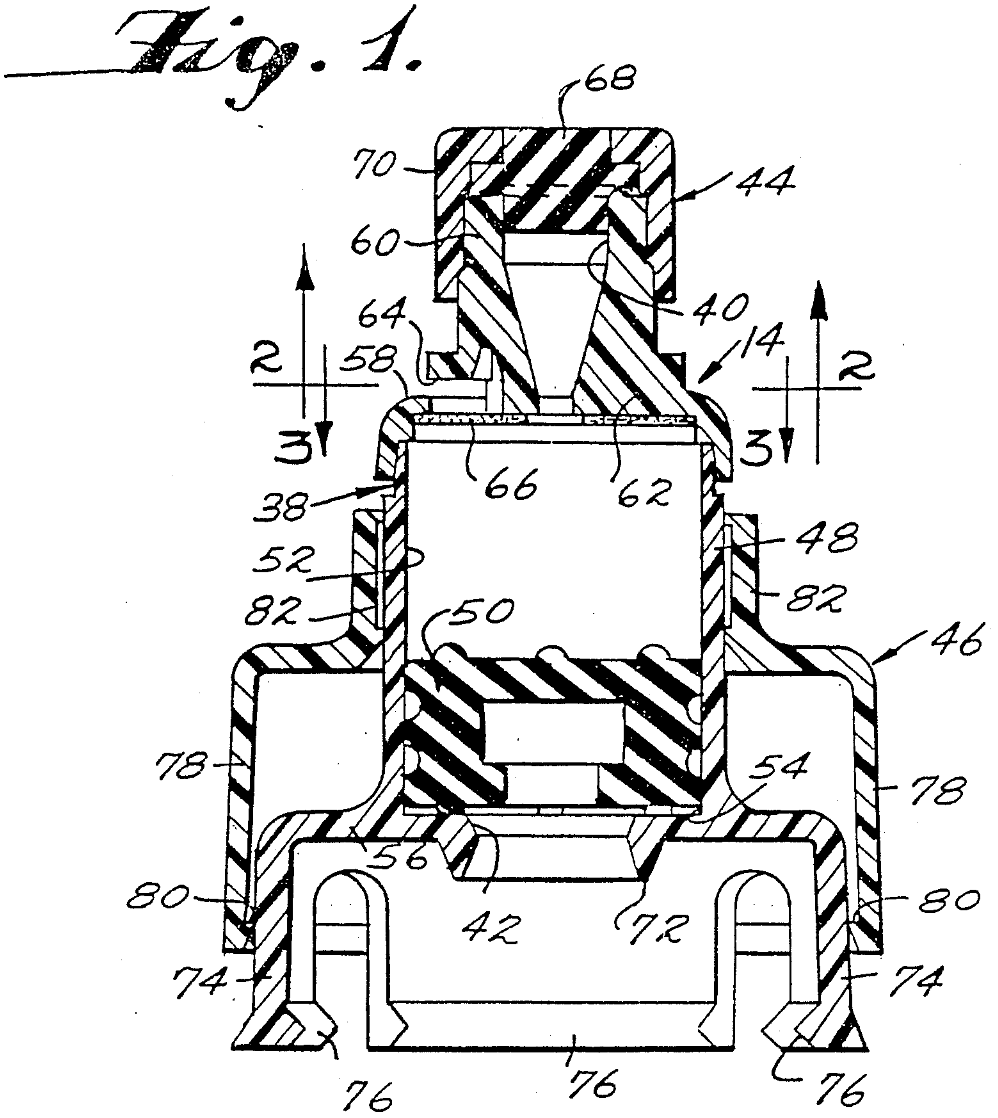
FIG. 1 is a vertical sectional view of a control assembly embodying the principles of the present invention.
Figure 2:
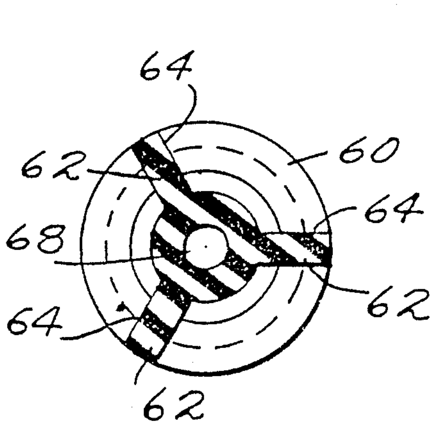
FIG. 2 is an sectional view taken along the line 2—2 of FIG. 1.
Figure 3:
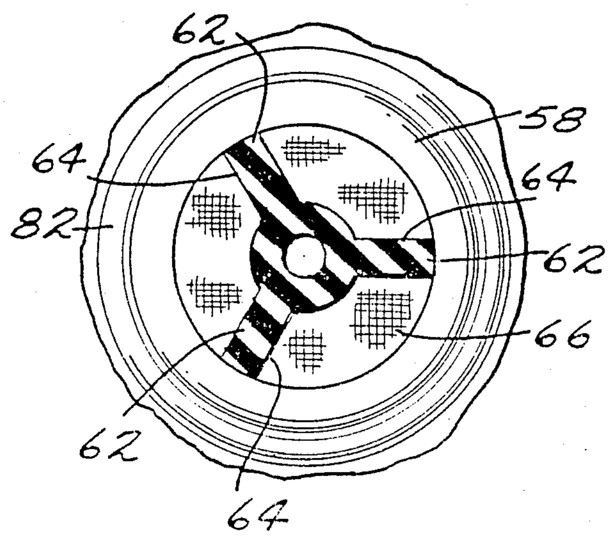
FIG. 3 is a fragmentary sectional view taken along the line 3—3 of FIG. 1.

In order to latchingly secure the bead 76 in the operative position, the attaching assembly 46 further includes an annular sleeve 78 having a latching barb 80 formed on the lower inner periphery thereof. The upper portion of the sleeve 78 includes an inwardly directly L-shaped flange 82 which serves to slidably mount the sleeve 78 on the cylindrical wall 48. The sleeve 78 is movable from an inoperative position, as shown in FIG. 1, downwardly into an operative position, as shown in FIGS. 4–7, wherein the latching barb 80 extends under the adjacent lower exterior periphery of the slotted skirt 74. Once in the operative position, the sleeve 78 cannot be readily moved back upwardly and the control assembly 14 is thus fixedly secured to the vial 12 in an operative position in such a way that it will be retained thereon for disposal with the vial after the same has been used.

In use, it is contemplated that the control assembly 14 would be provided to the user in a separate sterile package. The user would open the package with the control assembly 14 in the condition shown in FIG. 1. In this condition, the user simply grasps the tubular structure 38 and moves the slotted skirt 74 over the stopper assembly 26 of the vial 12 until the beads 76 engage beneath the same. Thereafter, the sleeve 78 is moved downwardly until the latching barb 80 engages beneath the bottom surface of the skirt 74. With the apparatus thus constituted, there are several modes of use depending upon whether the dosage of hazardous material 24 within vial container 18 is a one-dosage amount or a multiple dosage amount. Assuming it to be a single dosage amount and assuming the situation where the user who is to constitute the solution is also the person to use the solution after it is constituted, a typical use is set forth below:

As previously indicated, the apparatus 10 is arranged to be used with the diluent syringe 16. As shown in FIGS. 4–7, the syringe 16 includes the usual glass barrel 84 defining a chamber 86 which communicates at one end with a hypodermic needle 88 having a sharpened open end 90. A plunger 92 is slidably sealingly mounted in the syringe chamber 86. As shown in FIG. 4, the syringe plunger 92 has been actuated to draw a dosage amount of diluent 94 into the syringe chamber 86. With the apparatus 10 in the position shown in FIG. 4, the diluent syringe 16 containing a full dosage of diluent 94 in the chamber 86 thereof is aligned with the control assembly 14 with the open end 90 of the needle 88 in a position to pierce through the septum 68. By pushing down on the syringe 16, the needle end 90 is penetrated first through the septum 68 and then through the central portion of the piston 50 and finally through the central portion 32 of the elastomeric stopper 30 of the vial 12. The operator then depresses the syringe plunger 92 so as to eject the diluent 94 from the syringe chamber 86 through the open end 90 of the hypodermic needle 88 into the medicament chamber 28 of the vial container 18 to be intermixed with the hazardous material powder 24 therein.

FIG. 5 illustrates the condition of the syringe and apparatus 10 after the diluent 94 has been ejected from the syringe chamber 86 and injected into the medicament chamber 28 in the vial container 18. As shown, the medicament chamber 28 has a dosage of liquid medicament solution 96 in the lower portion thereof and a gaseous fluid 98 which includes saturated vapor of the hazardous material solution thereabove, both of which are retained under elevated pressure conditions by virtue of the added volume of the diluent. The syringe 16 with the plunger 92 held in fully engaged position is retained with the needle 88 in its penetrating relation as shown in FIG. 5, and, if necessary, the vial is agitated to complete the mixing procedure required to constitute the solution 96. Thereafter, the user simply inverts the entire apparatus 10 with the syringe 16 maintained in penetrating relation and then releases the plunger. The gaseous fluid 98 within the container remains on top of the liquid solution 96 and the pressure thereof serves to move the liquid medicament 96 from the vial container 18 into the open end 90 of the syringe needle 88, thus filling the syringe chamber 86 as the syringe plunger 92 moves downwardly. Where the liquid medicament 96 is to be injected directly into the patient, preferably, prior to withdrawal of the needle 88, the operator applies a slight pressure to the plunger 92 so as to ensure that any air in the interior of the needle 88 is discharged therefrom and into the vial container 18. This pressure is retained during the withdrawal of the needle from the elastomeric stopper 30 and immediately after such withdrawal, the pressure on the plunger 92 is relieved. During the withdrawal of the needle 88 from the elastomeric stopper, any residual pressure within the vial container which would tend to cause aerosoling of hazardous material from the interior of the vial container 18 past the elastomeric stopper 30 is contained within the sealed chamber 54 on the lower side of the piston 50. At the same time, any tendency for the manual pressure acting on the syringe plunger to eject a slight amount of additional liquid mixture from the needle before such manual pressure is relieved will result in such liquid being injected into the sealed chamber 54 controlled by the piston 50. Moreover, as the pressure conditions within the chamber 54 increase, the piston 50 moves away from its initial position in engagement with the annual wall 56 toward its final position. The frictional contact of the periphery of the piston 50 is chosen so that its frictional resistance is slightly greater than the frictional resistance to the movement of the hypodermic needle 88 in sealing relation through the central portion of the piston 50. Of course, this frictional resistance to the movement of the piston prevents the piston from exactly equalizing the pressure conditions in the chambers 52 and 54 on both sides thereof. However, the pressure equalization is a substantially equal one. In this regard, it will be noted that the pressure in the chamber 52 above the piston will at all times be equal to atmosphere through the vent openings 64 and the filter 66 does not provide any pressure seal but merely serves to prevent passage of hazardous material in solution from this portion of the chamber.

It can be seen from the above that, in a typical situation where a single syringe is used both as a reconstituting syringe and as a dosage syringe, the arrangement provided insures against hazardous material reaching the vented chamber 52. This insurance is provided by utilizing the pressure in the medicament chamber 28 to fill the syringe chamber 86 thus insuring that a minimum pressure will exist in the vial chamber 28 when the needle 88 is withdrawn from the vial stopper 30. In this way, any residual pressure which is transferred to the sealed chamber 54 will necessarily be of a low value capable of being handled by the relative movement of the piston 50.

Figure 7:
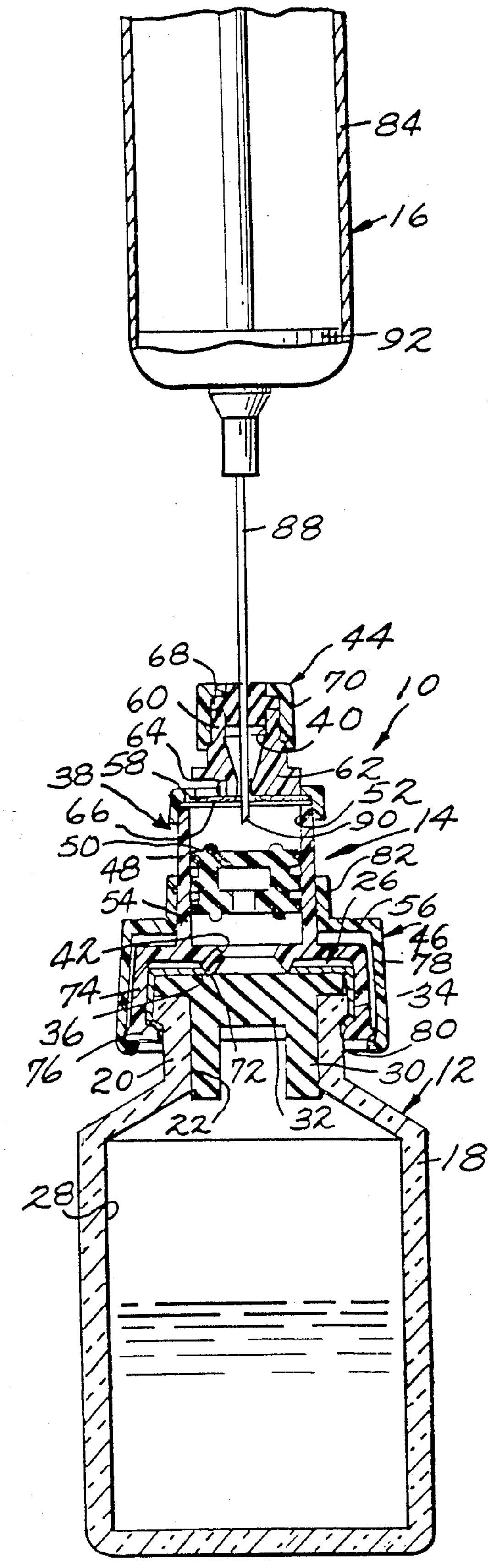
FIG. 7 is a view similar to FIG. 6 illustrating the next step of the method.

In situations where the reconstituting procedures are separated from the filling and injecting procedures, a typical mode of use in accordance with the principles of the present invention is set forth below, assuming first a one dosage vial 12 in the apparatus 10. The reconstituting procedure involves moving the needle 88 of the diluent syringe 16 through the septum 68, the piston 50, and the elastomeric stopper 30 in the manner previously described and shown in FIG. 4. Thereafter, the syringe plunger 92 is depressed to eject the diluent 94 from the syringe chamber 86 through the open end 90 of the syringe needle 88 into the vial chamber 28 provided by the vial container 18. When this movement of diluent has been completed as shown in FIG. 5, the user simply releases the plunger 92 with the vial 12 retained in its upright position so that the liquid 96 is in the lower portion of the vial chamber 28 and the open end 90 of the needle 88 is in communication with the gaseous fluid 98 within the vial chamber 28. By relieving the manual pressure acting on the syringe plunger 92, the gaseous fluid pressure within the vial chamber 28 thus communicates through the open end of the needle with the syringe chamber 86 moving the syringe plunger 92 upwardly until the pressure conditions are substantially equal and atmospheric. Here again, it will be understood that the syringe plunger 92 has frictional contact within the barrel 84 so that in the absence of a manual movement at the end, the syringe plunger 92 will reach a position where only substantial atmospheric conditions are obtained. The condition of the syringe 16 and apparatus 10 after this procedure has been accomplished is shown in FIG. 6 and it can be seen that the syringe chamber 86 of the diluent syringe is now occupied by a portion of the gaseous fluid 98 from the vial chamber 28 which may contain hazardous material. The operator then withdraws the syringe needle from the elastomeric stopper 30 and the piston 50 so that the open end 90 of the needle 88 is in communication with the vented chamber 52 as shown in FIG. 7. During this movement, any residual pressure within the vial chamber 28 which may aerosol therefrom is caught and sealed within the sealed chamber 54, as aforesaid. The operator then depresses the syringe plunger 92 to move the same into its fully engaged position and eject the gaseous fluid 96 from the chamber 86 through the open end 90 of the needle 88 into the vented chamber 52, as is also shown in FIG. 7. This gaseous fluid 98 basically is air with perhaps some hazardous material entrained therein. The air is allowed to pass through the filter 66 and outwardly through the vent openings 64 while the filter 66 prevents the passage of hazardous material outwardly of the chamber. After the gaseous fluid has been ejected from the syringe chamber 86, the syringe needle 88 is then withdrawn from the septum 68. In this way, the vial 12 with the control assembly 14 still engaged thereon is in a condition to be transported to the position of use, it being noted that the gaseous fluid 98 and liquid medicament 96 are now contained within the vial chamber 28 at substantially atmospheric pressure conditions.

When it is desired to utilize the liquid medicament 96 of the vial, a dosage syringe similar to the diluent syringe is initially moved into a position wherein the syringe plunger is disposed from its fully engaged position to an extent such that the volume within the syringe chamber 86 defined by the plunger 92 is generally equal to the volume of the dosage. Thus, this volume of the dosage syringe chamber 86 is initially filled with air. With the dosage syringe in this condition, the needle 88 is penetrated through the septum 68, the piston 50, and the elastomeric stopper 30 until the open end 90 thereof communicates with the interior of the vial chamber 28. The syringe plunger 92 is then depressed so as to inject the air within the syringe chamber 86 through the open end 90 of the needle 88 and into the vial chamber 28 thus raising the pressure conditions therein. The apparatus 20 including the vial 12 is then inverted and the operator releases the syringe plunger allowing the gaseous fluid pressure conditions acting on top of the liquid medicament 96 within the vial chamber 28 to pass into the open end 90 of the needle 88 and into the syringe chamber 86 moving the syringe plunger 92 downwardly, as aforesaid. Here again, basically the syringe plunger should move into a position in which the pressure as between the syringe chamber and the vial chamber is equalized at or slightly above or near atmospheric conditions. Before withdrawing the needle where required by the nature of the injection to be made, the operator applies a slight pressure to the syringe plunger 92 insuring that any gaseous fluid in the needle is ejected therefrom. The syringe needle is withdrawn while the syringe is retained in this condition and immediately after withdrawal from the elastomeric stopper 30, the manual pressure on the syringe plunger is released. As previously indicated, any tendency for any residual pressure in the vial chamber 28 to cause aerosoling or any tendency of the manual pressure to cause ejection of the liquid from the open end 90 due to changing pressure conditions as the needle end 90 is withdrawn from the elastomeric stopper 30 will result merely in any hazardous material in the aerosol or in the ejectate passing into the sealed chamber 54 where it is sealed from and pressure equalized with respect to the vented chamber 52 by the action of the piston 50. Thereafter, the syringe 16 is pulled all the way out thus withdrawing the needle first from the piston 52 and then from the septum 68. In this way the injectate syringe 16 is now in a proper equilibrium condition to be used. It will be understood that the step of ejecting gaseous fluid from the needle within the vial chamber is undertaken in those situations where the liquid medicament is to be injected directly into the patient. Where the liquid medicament is to be injected into an intravenous bag, this step need not be undertaken and preferably is omitted.

It will be understood that the above procedures are easily carried out also with a multiple dosage vial forming a part of the apparatus except that the filling procedures are repeated for a number of times equal to the number of dosages.

It can be seen from the above that the method of the present invention has applicability only in those situations where a mixing is carried out in the vial between an ingredient originally within the vial container and an extraneously added ingredient. The two ingredients are, in the usual case, a powder material and a diluent. However, they may be two different liquid ingredients.

The method is performed in those situations where mixing is carried out as an initial and separate procedure from the subsequent filling and using procedures. Thus, while the method is applicable only to the initial mixing procedure, the apparatus is useful in carrying out not only the initial mixing procedure but the separate final procedures as well. Consequently, the apparatus aspects of the present invention have applicability in situations where the procedures for manufacturing the final liquid medicament are carried out in the factory. Stated differently, the present invention contemplates market availability of the apparatus with the medicament in liquid form. Where the control assembly is marketed separately, it would have use with vials containing a premixed solution containing hazardous material. Hazardous material in this context means any material which it is desired to exclude from entering the environment.

It is important to note the difference between the material which is discharged into the filter vented chamber 52 when the method of the present invention is carried out and the material which aerosols into the sealed chamber 54 when a needle is withdrawn from the elastomeric stopper assembly 26. The material which is discharged into the filter vented chamber 52 is solely the atmosphere within the vial except for residual diluent or air which may remain in the diluent syringe after the diluent has been expelled into the vial. The aerosol also consists of the atmosphere but more importantly, liquid solution containing hazardous material located at the juncture between the exterior periphery of the needle and the interior surface of the central portion 32 of the stopper 30 engaging the same which may be moved outwardly by the atmosphere under pressure within the vial when the needle is withdrawn. The existence of solution at the aforesaid location is particularly prevalent during the filling operation because the vial container is inverted t effect filling so that the location is at the lowermost level of the liquid solution. If the needle is withdrawn while the vial is inverted, the existence of liquid at the location is almost assured. Even when the vial is moved back into its upright position before needle withdrawal, some liquid solution will remain in the location by surface adhesion. It is this additional hazardous material containing liquid solution which is contained in the aerosol which is not contained in the atmosphere discharged into the filter vented chamber 52 which is sealed from the filter vented chamber by the operation of the present invention.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. In a method of mixing a diluent with hazardous material sealingly enclosed by an elastomeric stopper assembly within a vial chamber of a vial in which a gaseous fluid under pressure is created within the vial chamber in communication with the liquid diluent and hazardous material mixed therein, the improvement which comprises, relieving the pressure of the gaseous fluid in the vial chamber while preventing hazardous material contained in the fluid from entering the immediate atmospheric environment, said fluid pressure relief being accomplished with the use of a syringe having an open ended hypodermic needle on one end of a cylindrical chamber within which a plunger is slidably sealingly mounted and a control assembly mounted on the vial so as to provide a control chamber sealed by a septum, said control chamber is capable of receiving a volume of hazardous material containing gaseous fluid under pressure and of retaining the gaseous fluid substantially at atmospheric conditions and preventing any hazardous material contained in the gaseous fluid from passing outwardly of the control chamber, said fluid pressure relief comprising the steps of communicating the open end of the syringe needle disposed in penetrating relation through the control assembly septum and the vial elastomeric stopper assembly with the gaseous fluid under pressure within the vial chamber with the syringe plunger fully engaged within the syringe chamber, maintaining said communication until the syringe plunger is withdrawn from said fully engaged position into an intermediate position so that sufficient gaseous fluid from the vial chamber passes into the syringe chamber through the open end of said syringe needle without the passage of liquid dosage to reduce the pressure of the gaseous fluid in the vial chamber and in the syringe chamber to a common pressure which is at most substantially equal to atmospheric pressure, withdrawing the syringe needle from the vial elastomeric stopper assembly while the syringe plunger is maintained in said intermediate position, moving the syringe plunger from said intermediate position into its fully engaged position with the open end of the syringe needle in communicating relation with said control chamber so as to expel the gaseous fluid contents of the syringe chamber through the open end of said syringe needle into said control chamber, and withdrawing the syringe needle from said control chamber with the syringe plunger in its fully engaged position after the gaseous fluid contents of the syringe chamber have been expelled through the open end of said syringe needle into said control chamber.

2. The method as defined in claim 1, wherein a dosage of the liquid solution of hazardous material and diluent in said vial chamber is subsequently filled within a dosage syringe having a dosage chamber with a plunger mounted therein and a syringe needle with an open end communicating therein by carrying out the following steps: utilizing a dosage syringe in which the dosage syringe plunger is in a starting position displaced from a fully engaged position and the volume of the dosage syringe chamber is filled with air which the volume of the dosage syringe chamber when said dosage syringe plunger is in said starting position being generally equal to the volume of the dosage to be filled, penetrating the dosage syringe needle through the control chamber septum and the elastomeric stopper assembly of the vial while the dosage syringe plunger is maintained in said starting position, moving the dosage syringe plunger from said starting position into said fully engaged position to thereby expel the air from the dosage syringe chamber through the open end of the dosage syringe needle into said vial chamber to thereby increase the pressure conditions within the vial chamber, utilizing the gaseous fluid pressure within the vial chamber to assist in the movement of an amount of liquid solution from within the vial chamber through the open end of the dosage syringe needle and into the dosage syringe chamber.

3. The method as defined in claim 2, wherein after the dosage of liquid solution has been moved into said dosage syringe chamber, the dosage syringe plunger is moved by manual pressure while the open end of the dosage syringe needle is disposed within the vial chamber to expel therefrom any gaseous fluid within the dosage syringe needle into the vial chamber.

4. The method as defined in claim 3, wherein the dosage syringe needle is withdrawn from the elastomeric stopper assembly of the vial after the expulsion of the gaseous fluid from the dosage syringe needle has been accomplished and thereafter the dosage syringe needle is withdrawn from the control chamber septum without any manual pressure being applied to the dosage syringe plunger.

5. The method as defined in claim 4, wherein said manual pressure is maintained on dosage syringe plunger until the dosage syringe needle is withdrawn from the elastomeric stopper assembly of the vial and thereafter immediately removed.

6. The method as defined in claim 5, wherein the gaseous fluid contents of the first mentioned syringe chamber expelled into said control chamber are maintained under atmospheric pressure conditions within said control chamber by communicating a vented portion of the control chamber to the atmosphere through a vent opening, the hazardous material in said expelled gaseous fluid being prevented from passing outwardly of the vented portion of the control chamber by a filter in the vent opening.

7. The method as defined in claim 6, wherein aerosoling which may take place as a result of residual pressure within said vial chamber when either said first mentioned syringe needle or said dosage syringe needle is withdrawn from the elastomeric stopper assembly of the vial is maintained within a sealed portion of the control chamber which is sealed from the vented portion communicating with the vent opening by a pressure equalizing piston.

8. The method as defined in claim 1, wherein the gaseous fluid contents of said syringe chamber expelled into said control chamber are maintained under atmospheric pressure conditions within said control chamber by communicating a vented portion of the control chamber to the atmosphere through a vent opening, the hazardous material in said expelled gaseous fluid being prevented from passing outwardly of the vented portion of the control chamber by a filter in the vent opening.

9. The method as defined in claim 8, wherein aerosoling which may take place as a result of residual pressure within said vial chamber when said syringe needle is withdrawn from the elastomeric stopper assembly of the vial is maintained within a sealed portion of the control chamber which is sealed from the vented portion communicating with the vent opening by a pressure equalizing piston.

* * * * *